(12) United States Patent
Murray et al.

(10) Patent No.: US 7,770,726 B2
(45) Date of Patent: *Aug. 10, 2010

(54) CATHETER PRODUCT PACKAGE AND METHOD OF FORMING SAME

(75) Inventors: Michael Murray, Ballina (IE); Kai Jorgensen, Copenhagen (DK)

(73) Assignee: Hollister Incorporated, Libertyville, IL (US)

( * ) Notice: Subject to any disclaimer, the term of this patent is extended or adjusted under 35 U.S.C. 154(b) by 233 days.

This patent is subject to a terminal disclaimer.

(21) Appl. No.: 11/760,545

(22) Filed: Jun. 8, 2007

(65) Prior Publication Data

US 2007/0289887 A1    Dec. 20, 2007

Related U.S. Application Data

(60) Provisional application No. 60/811,824, filed on Jun. 8, 2006.

(51) Int. Cl.
  B65D 83/10    (2006.01)
  B65D 81/24    (2006.01)
  A61B 19/02    (2006.01)
  A61M 5/00    (2006.01)
  A61M 25/00    (2006.01)

(52) U.S. Cl. ............ 206/364; 206/210; 206/438; 604/172; 604/265; 604/544

(58) Field of Classification Search ............ 206/364, 206/570, 571, 210, 438; 604/172, 219–222
See application file for complete search history.

(56) References Cited

U.S. PATENT DOCUMENTS 2,360,597 A * 10/1944 Topolski ............ 229/87.05
2,947,415 A     8/1960 Garth ............ 206/63.2
3,012,481 A    12/1961 Hughes
3,035,691 A     5/1962 Rasmussen et al.

(Continued)

FOREIGN PATENT DOCUMENTS

CH     677094     4/1991

(Continued)

OTHER PUBLICATIONS

International Search Report from PCT/US2007/070783, mailed Mar. 31, 2008 (5 pages).

(Continued)

*Primary Examiner*—Mickey Yu
*Assistant Examiner*—Chun Cheung
(74) *Attorney, Agent, or Firm*—Marshall, Gerstein & Borun LLP

(57) ABSTRACT

A sheet material wrapped about a catheter to form a package. The catheter extends generally longitudinally within the package, and the sheet material extends from a point beyond the proximal end to a point beyond the distal end of the catheter. Confronting proximal end edges, distal end edges and side edges of the sheet material are joined by a seal to define a sealed cavity. The sheet material has a tear strip affixed thereto which causes the package to open along an intended opening line. A gas permeable, liquid impermeable barrier divides the sealed cavity into a first compartment within which the catheter is contained and a second compartment within which a wick wetted with an aqueous liquid is entirely confined.

48 Claims, 7 Drawing Sheets

U.S. PATENT DOCUMENTS

| | | | |
|---|---|---|---|
| 3,291,377 A * | 12/1966 | Eggen | 426/122 |
| 3,460,529 A | 8/1969 | Leucci | 128/2 |
| 3,556,294 A | 1/1971 | Walck et al. | |
| 3,648,704 A | 3/1972 | Jackson | 128/349 R |
| 3,651,615 A | 3/1972 | Bohner et al. | |
| 3,736,805 A * | 6/1973 | Dent | 474/250 |
| 4,248,236 A | 2/1981 | Linder | |
| 4,290,526 A | 9/1981 | Haiss | 206/624 |
| 4,364,478 A * | 12/1982 | Tuns | 383/205 |
| 4,379,506 A | 4/1983 | Davidson | |
| 4,523,919 A | 6/1985 | Focke et al. | |
| 4,652,259 A | 3/1987 | O'Neil et al. | |
| 4,772,275 A | 9/1988 | Erlich | |
| 4,779,727 A | 10/1988 | Taterka et al. | |
| 4,811,847 A | 3/1989 | Reif et al. | |
| 4,838,429 A | 6/1989 | Fabisiewicz et al. | |
| 4,863,016 A | 9/1989 | Fong et al. | |
| 4,889,523 A | 12/1989 | Sengewald | |
| 4,923,061 A | 5/1990 | Trombley, III | |
| 4,925,448 A | 5/1990 | Bazaral | |
| 4,927,028 A | 5/1990 | Hemm et al. | |
| D311,064 S | 10/1990 | Utas-Sjoberg et al. | |
| 4,993,555 A | 2/1991 | Hemm | |
| 5,001,884 A | 3/1991 | Hanagata et al. | |
| 5,038,547 A | 8/1991 | Kai et al. | |
| D325,526 S | 4/1992 | Deguchi et al. | |
| 5,105,942 A | 4/1992 | van Veen et al. | |
| 5,147,341 A | 9/1992 | Starke et al. | |
| 5,165,540 A | 11/1992 | Forney | |
| 5,184,771 A | 2/1993 | Jud et al. | |
| 5,203,935 A | 4/1993 | May et al. | |
| 5,217,114 A | 6/1993 | Gadberry et al. | |
| 5,226,530 A | 7/1993 | Golden | |
| 5,322,163 A | 6/1994 | Foos | |
| 5,328,848 A | 7/1994 | Fong et al. | |
| 5,356,068 A | 10/1994 | Moreno | |
| 5,372,254 A | 12/1994 | Gross | |
| 5,454,798 A | 10/1995 | Kubalak et al. | |
| 5,470,419 A | 11/1995 | Sasaki et al. | |
| 5,497,601 A | 3/1996 | Gonzalez | |
| 5,501,341 A | 3/1996 | Van Es | |
| 5,582,342 A | 12/1996 | Jud | |
| 5,836,697 A | 11/1998 | Chiesa | |
| 5,848,691 A | 12/1998 | Morris et al. | |
| 5,895,374 A | 4/1999 | Rodsten | |
| D416,477 S | 11/1999 | Flint | |
| 6,004,305 A | 12/1999 | Hursman et al. | |
| 6,053,313 A | 4/2000 | Farrell et al. | |
| 6,053,905 A * | 4/2000 | Daignault et al. | 604/544 |
| 6,059,107 A | 5/2000 | Nøsted et al. | 206/364 |
| 6,065,597 A | 5/2000 | Pettersson et al. | |
| 6,098,800 A | 8/2000 | Bennish, Jr. et al. | 206/439 |
| 6,185,907 B1 | 2/2001 | Malin et al. | |
| 6,228,458 B1 | 5/2001 | Pinchen et al. | |
| 6,409,717 B1 | 6/2002 | Israelsson et al. | |
| 6,415,921 B2 | 7/2002 | Ye et al. | |
| 6,457,863 B1 | 10/2002 | Vassallo | |
| D467,079 S | 12/2002 | Willows et al. | |
| 6,499,278 B2 | 12/2002 | Cronauer et al. | |
| 6,634,498 B2 | 10/2003 | Kayerød et al. | 206/364 |
| 6,736,805 B2 | 5/2004 | Israelsson et al. | |
| D491,803 S | 6/2004 | Nestenborg et al. | |
| 6,745,545 B2 | 6/2004 | Schneider et al. | |
| D496,266 S | 9/2004 | Nestenborg et al. | |
| D497,205 S | 10/2004 | Kubalak et al. | |
| D498,671 S | 11/2004 | Nestenborg et al. | |
| D498,672 S | 11/2004 | Nestenborg et al. | |
| D499,016 S | 11/2004 | Nestenborg et al. | |
| D499,017 S | 11/2004 | Nestenborg et al. | |
| D499,335 S | 12/2004 | Nestenborg et al. | |
| D499,643 S | 12/2004 | Nestenborg et al. | |
| 6,848,574 B1 | 2/2005 | Israelsson et al. | |
| 6,848,591 B2 | 2/2005 | Kiel et al. | |
| D503,335 S | 3/2005 | Risberg et al. | |
| 6,884,206 B2 | 4/2005 | Lasson et al. | |
| D505,067 S | 5/2005 | Nestenborg et al. | |
| 6,974,032 B2 | 12/2005 | Intini et al. | |
| 6,996,952 B2 | 2/2006 | Gupta et al. | 53/434 |
| 7,334,679 B2 * | 2/2008 | Givens, Jr. | 206/364 |
| 7,380,658 B2 * | 6/2008 | Murray et al. | 206/364 |
| 7,476,223 B2 * | 1/2009 | McBride | 604/544 |
| 2001/0054562 A1 | 12/2001 | Pettersson et al. | 206/364 |
| 2003/0008042 A1 | 1/2003 | Khalsa et al. | |
| 2003/0034264 A1 | 2/2003 | Hamai et al. | |
| 2003/0035868 A1 | 2/2003 | Coulter et al. | |
| 2003/0132128 A1 | 7/2003 | Mazur | |
| 2003/0168365 A1 * | 9/2003 | Kaern | 206/364 |
| 2003/0174909 A1 | 9/2003 | Parra | |
| 2004/0074794 A1 | 4/2004 | Conway et al. | |
| 2004/0136623 A1 | 7/2004 | Obara | |
| 2004/0142074 A1 | 7/2004 | Hentzel et al. | 426/106 |
| 2005/0003155 A1 | 1/2005 | Huffer | |
| 2005/0109648 A1 * | 5/2005 | Kerzman et al. | 206/364 |
| 2005/0194276 A1 | 9/2005 | Lubs et al. | 206/364 |
| 2006/0163097 A1 | 7/2006 | Murray et al. | 206/364 |

FOREIGN PATENT DOCUMENTS

| | | |
|---|---|---|
| DE | 10 324 012 | 12/2004 |
| EP | 0 440 427 | 8/1991 |
| EP | 0 492 399 | 7/1992 |
| EP | 0 521 618 | 1/1993 |
| EP | 0 677 299 A1 | 4/1995 |
| EP | 0 680 896 | 11/1995 |
| EP | 0 957 043 | 11/1999 |
| EP | 0 959 021 | 11/1999 |
| EP | 1 095 856 A2 | 5/2001 |
| EP | 1 120 355 | 8/2001 |
| EP | 1 262 425 | 12/2002 |
| EP | 1 346 917 | 9/2003 |
| EP | 1 447 345 | 8/2004 |
| GB | 1 465 544 | 2/1977 |
| GB | 2 235 680 | 3/1991 |
| GB | 2 284 764 A | 6/1995 |
| GB | 2 404 916 | 2/2005 |
| WO | WO-98/06642 | 2/1998 |
| WO | WO 99/42155 | 8/1999 |
| WO | WO 03/008029 A2 | 1/2003 |
| WO | WO-03/064279 | 8/2003 |
| WO | WO 2005/014055 A2 | 2/2005 |

OTHER PUBLICATIONS

Written Opinion from PCT/US2007/070783, mailed Mar. 31, 2008 (9 pages).

* cited by examiner

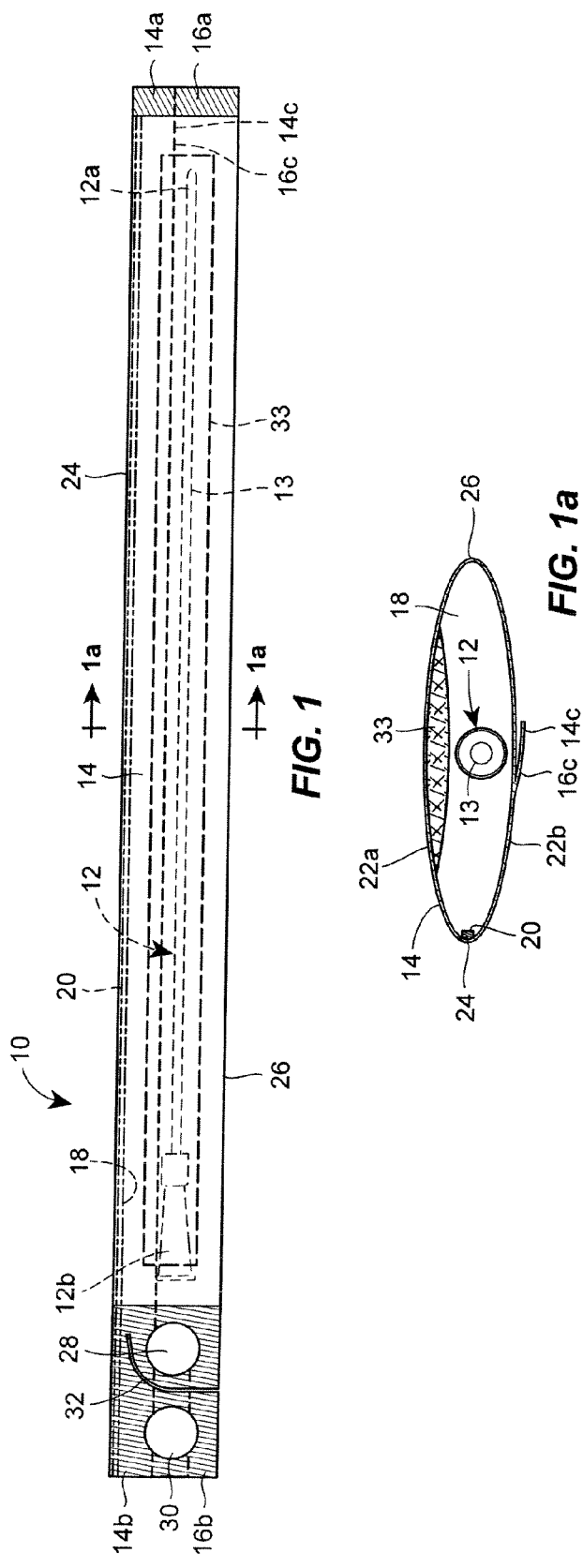
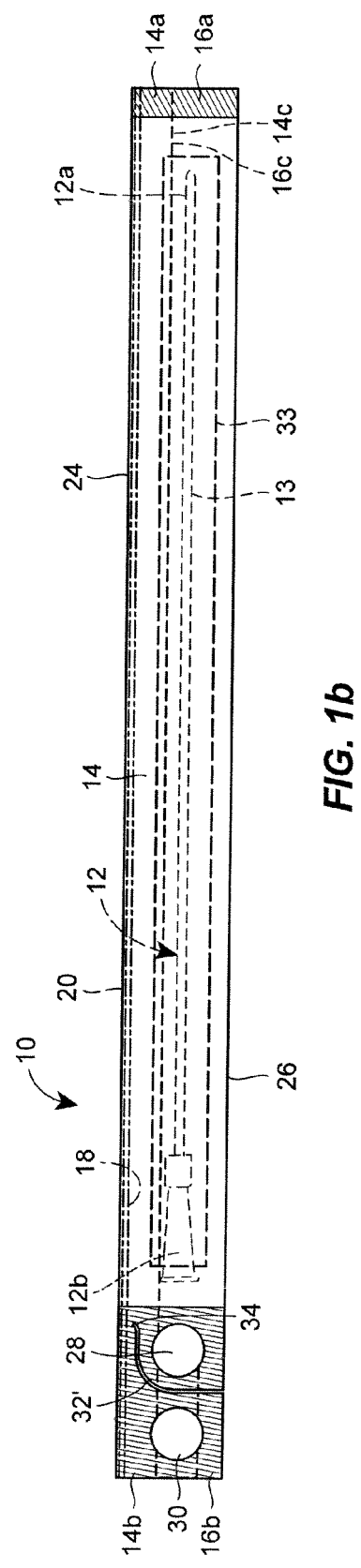

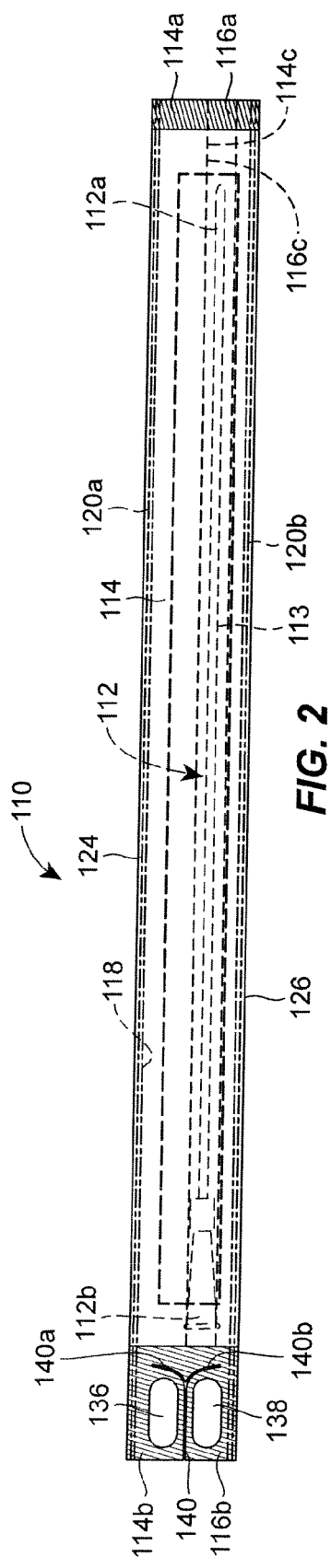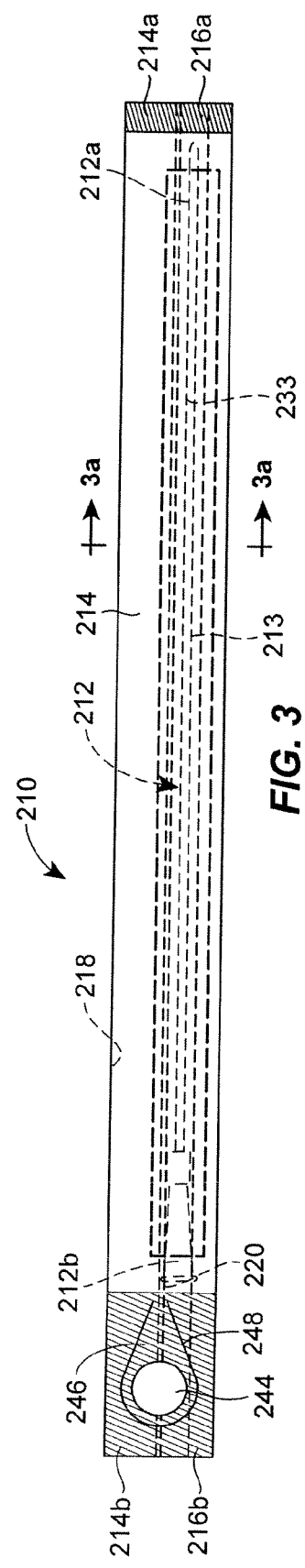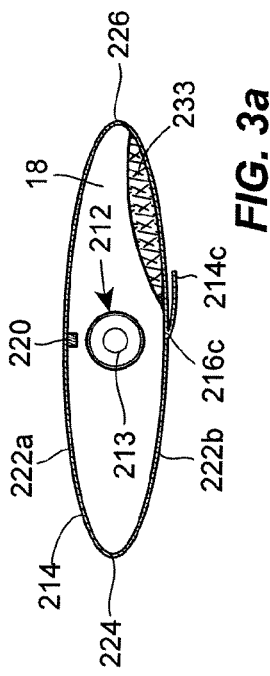

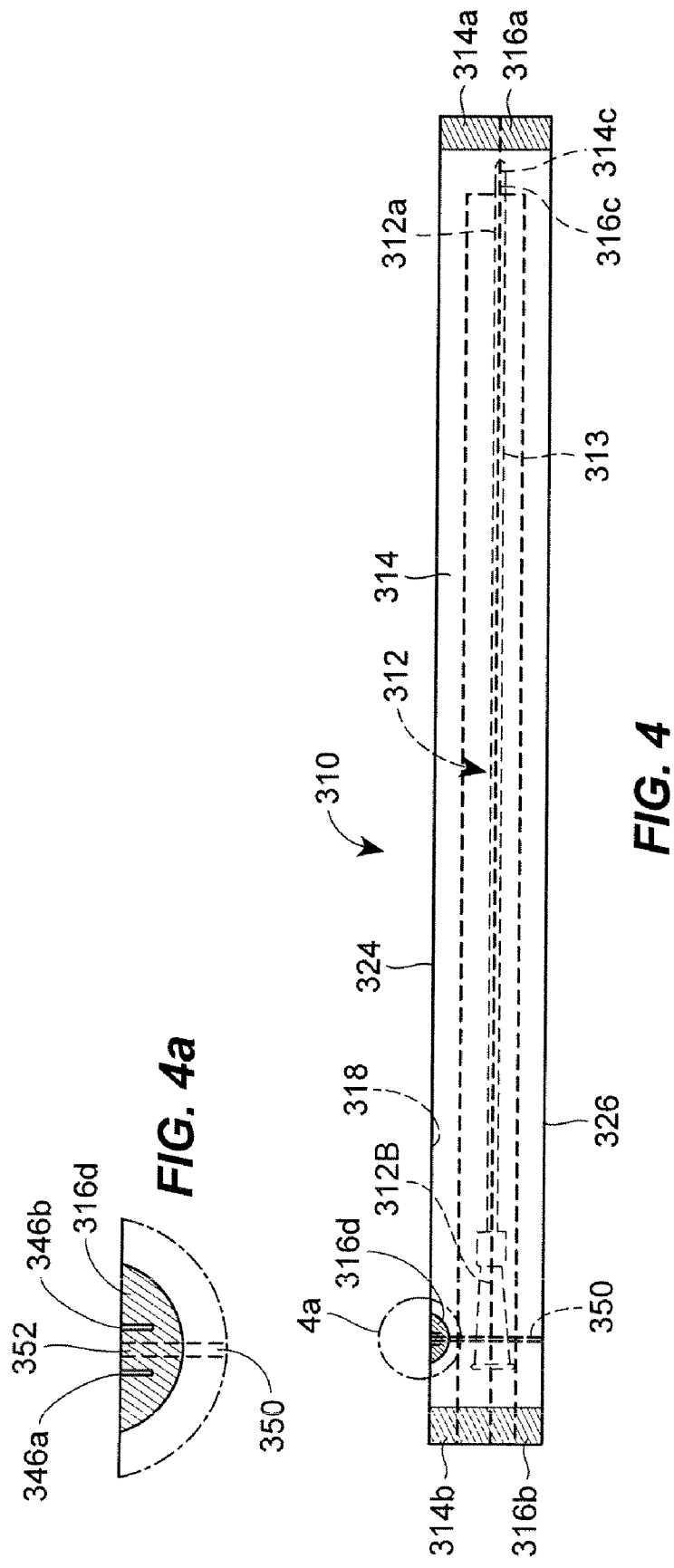

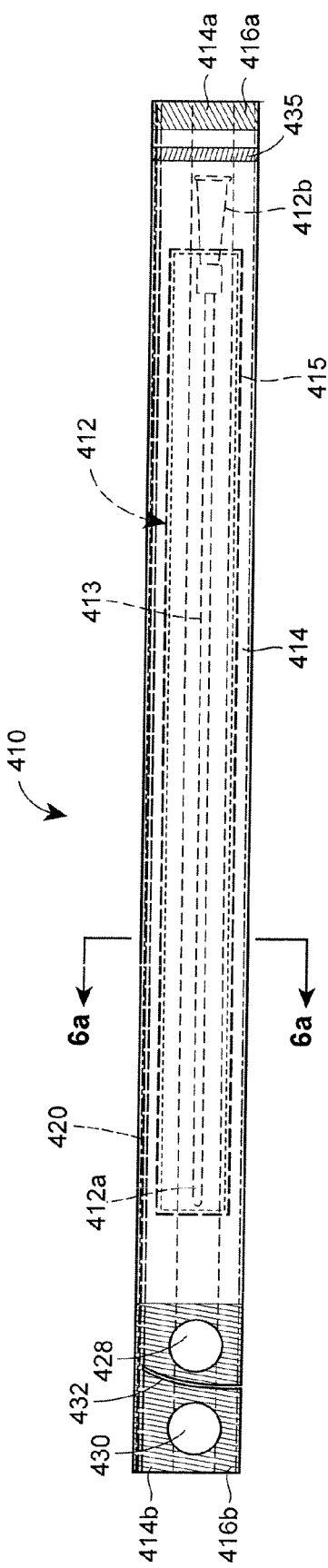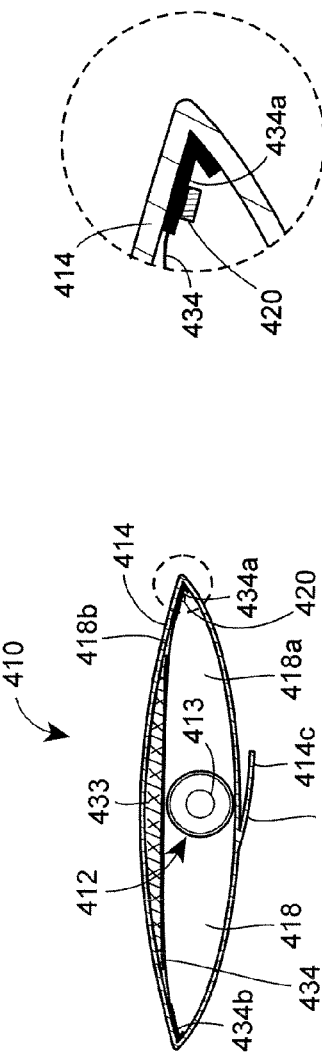
FIG. 6
FIG. 6b
FIG. 6a

CATHETER PRODUCT PACKAGE AND METHOD OF FORMING SAME

CROSS-REFERENCE TO RELATED APPLICATION

This application claims priority to U.S. Provisional Patent Application No. 60/811,824 filed Jun. 8, 2006.

FIELD OF THE DISCLOSURE

The present disclosure is generally related to catheter product packaging and, more particularly, to a catheter product package and method of forming same.

BACKGROUND

Intermittent catheterization is a good option for many who suffer from various abnormalities of the urinary system. Those with such abnormalities often find it desirable to use individually packaged, sterile catheters. Important criteria for such a single use product include the cost and ease of use in performing intermittent catheterization.

With regard to both cost and ease of use, these factors apply to both the catheter and the package for the catheter. Thus, it is important that end users find these criteria to be acceptable to enhance the desirability of intermittent catheterization.

Current intermittent catheters are packaged in such a way that the end user is usually required to touch the catheter in order to insert it into the urethra. It is notable in this connection that intermittent catheters are commonly provided with a surface treatment using a lubricant to reduce friction in order to allow for easier, less traumatic insertion and withdrawal. Currently, there are two major categories of intermittent catheters having lubricated surfaces, i.e., gel coated catheters and hydrophilic coated catheters.

Gel coated catheters are made easier to insert by having the user apply a gel to the catheter surface, or more conveniently, the gel can be supplied with the packaged catheter. Typically, a system may be provided with the packaged catheter in order to assist in applying the gel to the catheter surface. This system may be one where the gel is put onto the catheter surface just before or during the packaging operation, or one where the gel is applied to the surface as the catheter is being inserted by the user.

In a hydrophilic coated catheter, the catheter is typically provided with a thin hydrophilic coating which is adhered to the outer surface of the catheter for activation by contact with a hydrating liquid such as liquid water or saline solution. When the coating is activated by contact with liquid water or saline solution, it becomes slippery, creating a catheter surface that has an extremely low coefficient of friction. The most common form of this product is a sterile, individually packaged single use catheter provided in a dry state or condition. The user typically exposes the coating to contact with liquid water or saline solution, waits approximately 30 seconds or more, and then removes the catheter from the package in a condition in which it is ready for insertion. The waiting time of approximately 30 seconds or more during which the liquid water or saline solution is in contact with the coating is necessary to accommodate an induction period for activation of the coating. During the induction period, as the hydrophilic coating is activated (for example by soaking the catheter in liquid water or saline solution), the hydrophilic coating swells and causes the catheter surface to become lubricious.

In one version of the hydrophilic coated catheter, it is provided in a package that already contains enough loose liquid water to cause it to be fully immersed so the user need only open the package and remove the catheter ready for insertion without the need to add liquid water or saline solution and wait 30 seconds or more. Other new products provide the amount of liquid water or saline solution necessary for immersion of the catheter in a separate compartment of the package. With these products, one must open the separate compartment allowing the liquid water or saline solution to enter the catheter-containing chamber for direct contact with the hydrophilic coated surface. Depending on the characteristics of the product and packaging, and on the amount of liquid water or saline solution in the separate chamber, the user may be asked to manipulate the package to bathe the catheter surface in the hydrating liquid in order to activate the hydrophilic coating on the catheter surface.

In all of these existing hydrophilic coated catheter products, proper lubrication of the catheter depends upon direct contact of liquid water or saline solution with the entirety of the hydrophilic coated catheter surface for a definite period of time following which the catheter can be removed from the package ready for insertion into the urethra by the user.

With regard to both gel coated catheters and hydrophilic coated catheters, the package is important. The package must be formed of a material and in a manner which is sufficient to hold the gel coated catheter and gel, or the hydrophilic coated catheter and liquid water, for a commercially acceptable shelf life. This means that the package must hold these respective products with little or no deterioration to either the catheter or its lubricant for a period of time that renders the packaged catheter commercially acceptable. Typically such a package is formed of two sheets of a suitable material which hold the gel coated catheter and gel or the hydrophilic coated catheter and liquid water between them. The two sheets of material are conventionally secured together with an adhesive or by welding to form a seal that extends entirely about the perimeter of the package. With this understanding of available catheter packages, there is an important criterion that has yet to be satisfactorily addressed.

In particular, it is well known that many users of intermittent catheters are persons possessing a limited degree of manual dexterity. Thus, it is imperative that the package can be opened easily by the end user of either a gel coated, or a hydrophilic coated, catheter while also minimizing any risk of the gel contacting the user's hands or clothing or of the liquid spilling from the package. The present disclosure avoids these problems in a highly advantageous catheter package and method of forming same.

SUMMARY OF THE DISCLOSURE

The method of forming a package for a catheter product includes the step of providing a sheet material for the package. It also includes the steps of placing the catheter product on the sheet material and, thereafter, wrapping the sheet material around the catheter product. Further, the method includes the step of sealing the sheet material to form a sealed cavity with the catheter product disposed within the sealed cavity.

In one particularly suitable form, the seal comprises a single longitudinal seal preferably combined with a pair of end seals at opposite ends of the package and, additionally, the method may include the step of affixing a tear strip to the sheet material prior to, simultaneously with, or subsequent to, placing the catheter product on the sheet material.

In an advantageous form of the method, the step of affixing a tear strip to the sheet material includes affixing the strip to extend in a desired direction relative to the catheter product within the sealed cavity after the sheet material is sealed. Prior to the wrapping step, the catheter product and tear strip are both preferably on a common surface of the sheet material to extend in laterally spaced, and preferably in generally parallel relation in a longitudinal direction thereon. Further, the sheet material may advantageously comprise a liquid tight, gas impermeable foil, and the tear strip may be formed of any of a number of materials including polyethylene, polyester, or other materials, or a combination of materials. The tear strip may be adhesively or otherwise affixed to the common surface of the sheet material or it may be affixed by other means, e.g., the strip may have a polyethylene backing so it can be directly heat sealed to the sheet material. Preferably, the foil has sufficient aluminum content, or is otherwise provided with sufficient tear propagation properties, so that tearing in the direction of the tear strip causes the tear to thereafter propagate along the tear strip to cause the package to open along an intended opening line.

Alternatively, the package may be formed of a gas permeable material, provided the gas permeability would not compromise the required shelf life for the lubricant (i.e., the gel or liquid) and provided the gas permeability would not compromise the sterile delivery of the packaged catheter.

In any case, whether the material for the package is foil or some other material, it will be understood that the selected material should have the requisite linear tear propagation tendencies to facilitate easy opening of the package by the end user.

Further, the step of sealing the sheet material preferably includes forming a seal preferably generally parallel to the catheter product and forming a seal generally perpendicular to the catheter product at each of opposite ends thereof. It is, therefore, advantageous to form a longitudinal seal along the length of the catheter product and to form an end seal at each of opposite ends of the catheter product to form the sealed cavity for the catheter product. With the sheet material comprising a liquid tight, gas impermeable foil, the longitudinal seal and end seals are preferably all formed as weld seals with one of the end seals formed longer than the other of the end seals.

With the catheter product and tear strip both on a common surface of the sheet material, the tear strip preferably extends from one of the end seals to the other generally parallel to the longitudinal seal. Thus, the tear strip may advantageously be made to extend preferably generally parallel to the catheter product and also to the longitudinal seal, and it is also made to extend into each of the end seals. With one of the end seals formed longer than the other, the longer of the end seals preferably has a finger hole and a tear line extends from adjacent the finger hole to adjacent the tear strip. The catheter product may comprise a catheter having a hydrophilic coating in which case the method preferably includes affixing or otherwise disposing a wick, such as, for example, a fabric strip, an absorbent paper strip, an absorbent open-celled foam strip or anything else that will emit a vapor, on a common surface of the sheet material with the tear strip. The method then also advantageously includes wetting the wick with an aqueous liquid prior to forming the sealed cavity to thereafter produce a water vapor atmosphere within the sealed cavity to activate the hydrophilic coating. Preferably, the wick is disposed on the common surface of the sheet material to extend in preferably generally parallel relation to the catheter and also to the tear strip in a longitudinal direction on the sheet material.

Whenever a wetted wick is used to activate a hydrophilic coating, a gas permeable, liquid impermeable barrier may be advantageously heat sealed to the common surface of the sheet material to cover the wick. This barrier is preferably applied and heat sealed to the common surface of the sheet material shortly after the wick has been wetted with a suitable liquid. In this manner, the sealed cavity formed by the package will have the catheter product in one compartment and the liquid used to wet the wick in another compartment whereby the catheter product is maintained out of direct contact with the liquid.

In addition, it is believed to be desirable to adhesively or otherwise affix the tear strip to the heat seal along one of the longitudinal edges of the barrier. The compartment containing the wetted wick is liquid tight as a result of being heat sealed entirely about its perimeter to confine the liquid therein. Thus, the tear strip is affixed within the bounds of the heat seal so the compartment will remain liquid tight even after the package has been opened.

More specifically, the tear strip can be used to cause a tear to propagate along the tear strip to cause the package to open along an intended opening line which exposes only the compartment containing the catheter product and not the compartment containing the wick wetted with liquid.

In addition, the method of forming a package for a catheter is advantageous not only for use with catheters alone but also for catheters assembled within a urine collection bag. In the latter case, the principal difference will be that while the package is still generally rectangular in shape, the ratio of length to width for the package used for the catheter/collection bag product will be considerably less than for the package used for the catheter alone to accommodate the typical size and shape of a collection bag. Unlike the long, narrow shape of a typical catheter package, the catheter will be folded into a generally U-shape within the collection bag thereby requiring a shorter but wider package.

In an automated method, the sheet material is advanced from a roll in a flat form toward a catheter product receiving point, and the catheter products are advanced one at a time above the sheet material toward the catheter product receiving point. The tear strip is affixed to the sheet material as it advances toward the catheter product receiving point and the sheet material is wrapped into a U shape to receive the catheter products at the catheter product receiving point. The catheter products are placed on a conveyor that feeds the catheter products onto the U shaped sheet material one at a time at the catheter product receiving point, and the sheet material is then further wrapped to form a cavity. In addition, the automated method includes sealing the sheet material to form separate, sealed cavities, and thereafter cutting the sheet material to form separate, distinct packages for each of the catheter products.

In another respect, the present disclosure sets forth a package for a catheter product comprised of a sheet material wrapped about the catheter product to form a package for the catheter product. The catheter product preferably extends generally longitudinally within the package, and the sheet material extends from beyond the proximal end to beyond the distal end of the catheter product. The sheet material is wrapped about the catheter product to have confronting proximal end and distal end sheet edges and confronting side sheet edges. The confronting proximal end and distal end sheet edges and the confronting side sheet edges of the sheet material are joined by a seal to define a sealed cavity for the catheter product. In addition, a tear strip is affixed to the sheet material to cause the sheet material to tear along the tear strip to thereby cause the package to open along an intended opening line for access to the catheter product in the package.

Preferably, the tear strip extends within the sealed cavity in a desired direction relative to the catheter product to cause the package to open along the intended opening line in a manner facilitating removal of the catheter product from the package for use. The tear strip is advantageously affixed to an inner surface of the sheet material within the sealed cavity and extends from the sealed proximal end to the sealed distal end sheet edges in generally parallel relation to the catheter product. Alternatively, the tear strip is advantageously affixed to an inner surface of the sheet material within the sealed cavity and extends adjacent and generally parallel to one of the sealed proximal end and sealed distal end edges. In either case, the sheet material preferably comprises a liquid tight, gas impermeable foil, the tear strip is formed of a suitable material such as polyester having a polyethylene backing, and the tear strip is affixed in position within the sealed cavity on the inner surface of the sheet material.

In one embodiment, the package is of a generally rectangular shape, the sheet material is wrapped about the catheter product and sealed to define a front panel and a rear panel, and a longitudinal seal is formed in the middle of the rear panel. The tear strip is then affixed to an inner surface of the sheet material so as to be positioned in the middle of the front panel so as to be directly opposite the longitudinal seal formed in the middle of the rear panel. In another embodiment, the front and rear panels define a pair of parallel side edges and include a pair of tear strips affixed to an inner surface of the sheet material so that one of the tear strips is positioned at each of the side edges.

In still another embodiment, the front and rear panels define a pair of parallel side edges and include a single tear strip affixed to an inner surface of the sheet material near or adjacent to one of the side edges.

In still another embodiment, the seal joining the confronting side sheet edges forms a longitudinal seal preferably generally parallel to the catheter product and the seals joining the confronting proximal end and distal end sheet edges form end seals generally perpendicular to the catheter product. The sheet material again advantageously comprises a liquid tight, gas impermeable foil, the longitudinal seal and the end seals all are formed as weld seals, and one of the ends seals is formed longer than the other of the end seals. With one of the end seals being formed longer than the other, the longer of the end seals advantageously has at least one finger hole and a tear line extending from adjacent the finger hole to adjacent the tear strip to propagate tearing along the tear strip.

In still another embodiment, the catheter product comprises a catheter having a hydrophilic coating and the package includes a wick disposed on an inner surface of the sheet material within the sealed cavity containing the catheter. The wick is wetted with an aqueous liquid prior to forming the sealed cavity so as to thereafter produce a water vapor atmosphere within the sealed cavity to activate the hydrophilic coating on the catheter. Further, the wick is preferably disposed on the inner surface of the sheet material within the sealed cavity to extend in generally parallel relation to the catheter and the tear strip in a longitudinal direction thereon.

In this embodiment, a gas permeable, liquid impermeable barrier is advantageously heat sealed to the inner surface of the sheet material to cover the wetted wick. This barrier is preferably applied and heat sealed to the common surface of the sheet material shortly after the wick has been wetted with the liquid. In this manner, the sealed cavity formed by the package will have the catheter contained in one compartment and the liquid used to wet the wick will be entirely confined within another compartment. In an automated method for packaging this embodiment, the conveyor feeds the catheter onto the gas permeable, liquid impermeable barrier sealed to the sheet material, rather than directly onto the sheet material.

In addition, the tear strip is preferably affixed to the heat seal along one of the longitudinal edges of the barrier within the bounds of the heat seal so the compartment will remain liquid tight even after the package has been opened using the tear strip.

In still another embodiment, the package is formed for use with catheter products which comprise catheters folded into a generally U-shape and disposed within a urine collection bag. The principal difference in the packages will be the size and shape, i.e., while the package still will be generally rectangular in shape, the ratio of length to width for the catheter/collection bag package will be considerably less than for the package used for a catheter alone. Unlike the long, narrow shape of a typical catheter package, the catheter will be folded into a generally U-shape within the collection bag thereby requiring a shorter but wider package than for a catheter alone.

With regard to all of the aforementioned features of the package, it will be understood that they are useful for all catheter product packages regardless of the exact size and shape and whether or not they are formed to hold catheters alone or to hold catheter/collection bag assemblies.

In another respect, the catheter product package may be constructed of two sheets of material which are sealed about their perimeters to define a catheter product-receiving sealed cavity, or it may be constructed of a vacuum or thermo formed plastic material to define a cavity sealed with a sheet material. A tear strip may advantageously be affixed to the sheet material to cause it to tear along the tear strip so the package opens along an intended opening line whereby the tear strip extends from a perimeter seal to a point within the sealed cavity to facilitate removal of the catheter product from the package for use. Preferably, the tear strip is secured adhesively or by heat sealing it to an inner surface of the sheet material, and the sheet material is formed of foil or some other material having suitable linear tear propagation tendencies to cause the package to be opened along the intended opening line.

BRIEF DESCRIPTION OF THE DRAWINGS

FIG. 1 is a plan view of a package for a catheter product in accordance with the present disclosure;

FIG. 1a is a cross-sectional view of the catheter product package of FIG. 1 taken along the line 1a-1a;

FIG. 1b is a minor modification of the embodiment of catheter product package such as illustrated in FIG. 1;

FIG. 2 is a plan view of a second embodiment of catheter product package in accordance with the present disclosure;

FIG. 3 is a plan view of a third embodiment of a catheter product package in accordance with the present disclosure;

FIG. 3a is a cross-sectional view of the catheter product package of FIG. 3 taken along the line 3a-3a FIG. 4 is a plan view of a fourth embodiment of a catheter product package in accordance with the present disclosure;

FIG. 4a is a cut away view of a tear strip and opening tab for the embodiment illustrated in FIG. 4;

FIG. 6 is a plan view of a fifth embodiment of a catheter product package in accordance with the present disclosure;

FIG. 6a is a cross-sectional view of the catheter product package of FIG. 6 taken along the line 6a-6a;

FIG. 6b is an enlarged detail view of the balloon portion of FIG. 6a showing the positioning of the heat seal and tear tape;

FIG. 8a is a cross-sectional view of the catheter product package of FIG. 7 taken along the line 8a-8a.

DETAILED DESCRIPTION OF THE PRESENT DISCLOSURE

Figure 5:
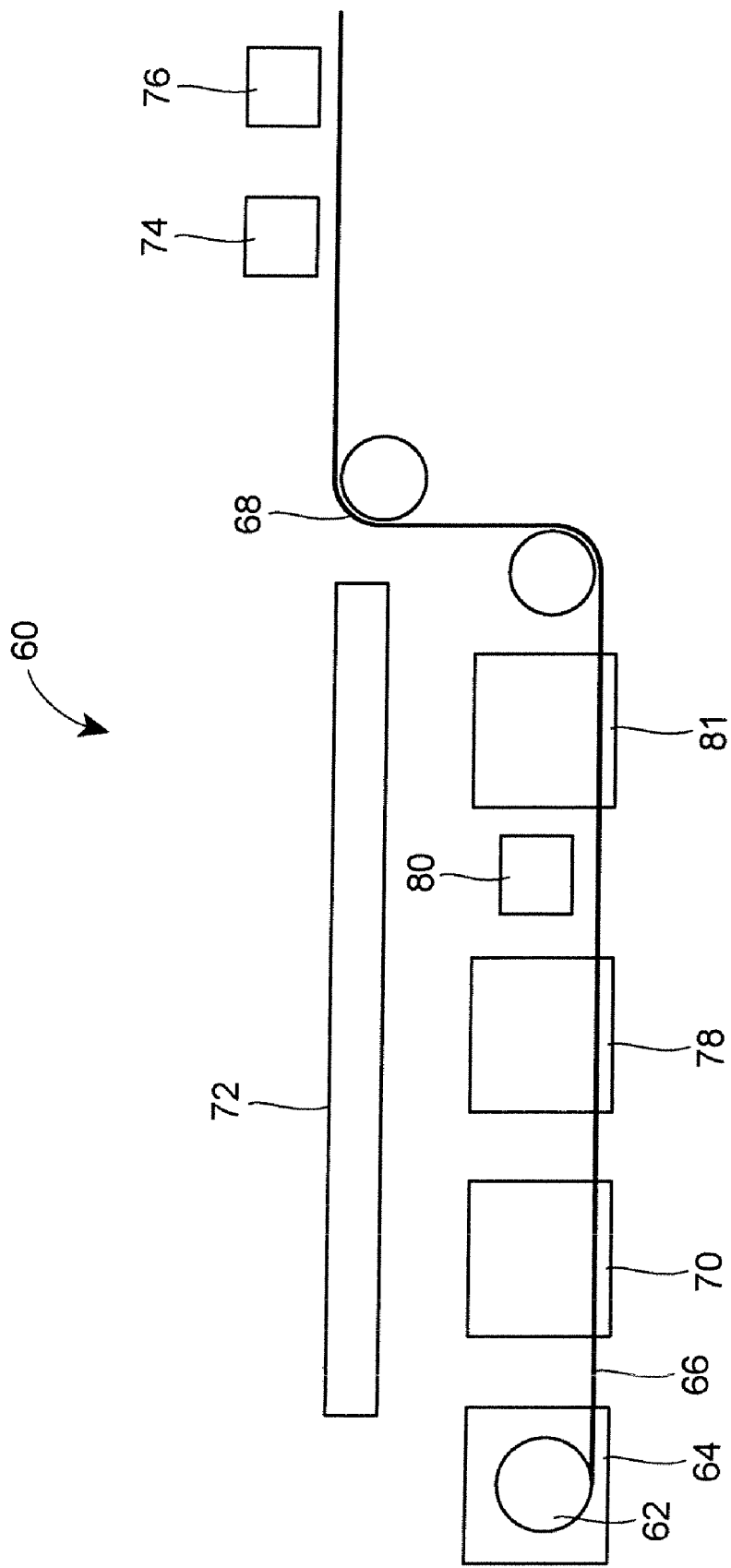
FIG. 5 is a schematic view of an automated method of forming a catheter product package in accordance with the present disclosure.

Referring to FIGS. 1 and 1a, the present disclosure comprises a package 10 for a catheter product 12 comprising a sheet material 14 wrapped about the catheter product 12 to form a package for the catheter product. The catheter product 12 extends generally longitudinally within the package 10, and the sheet material extends from beyond the proximal end 12a to beyond the distal end 12b of the catheter product 12. The sheet material 14 is wrapped about the catheter product 12 so as to have confronting proximal end 14a and distal end 14b sheet edges and confronting side sheet edges 14c. The confronting proximal end 14a and distal end 14b sheet edges and the confronting side sheet edges 14c of the sheet material 14 are sealed as at 16a, 16b, and 16c to define a sealed cavity 18 for the catheter product 12. Still referring to FIGS. 1 and 1a, a tear strip 20 is affixed to the sheet material 14 to cause the sheet material to tear along the tear strip 20 to thereby cause the package 10 to open along an intended opening line as defined by the tear strip 20.

As will be seen, the tear strip 20 extends within the sealed cavity 18 in a desired direction relative to the catheter product 12 to cause the package 10 to open along the intended opening line so as to facilitate removal of the catheter product 12 from the package 10 for use thereof. The tear strip 20 is adhesively or otherwise affixed to an inner surface of the sheet material 14 within the sealed cavity 18 and extends from the sealed proximal end 14a to the sealed distal end 14b sheet edges in generally parallel relation to the catheter product 12. With this arrangement, the sheet material 14 comprises a liquid tight, gas impermeable foil that may be coated with a heat seal layer, the tear strip 20 is formed of a suitable material such as polyester having a polyethylene backing, and the tear strip 20 is adhesively or otherwise affixed in position within the sealed cavity 18 on the inner surface of the sheet material 14.

From the foregoing, and FIGS. 1 and 1a, it will be appreciated that the package 10 is of a generally rectangular shape, the sheet material is wrapped about the catheter product 12 and sealed to define a front panel 22a and a rear panel 22b, and a single longitudinal seal 16c is formed in the middle of the rear panel 22b. It will therefore be appreciated that in the embodiment of FIGS. 1 and 1a the tear strip 20 is adhesively or otherwise affixed to the inner surface of the sheet material 14 so as to be positioned along one side edge of the package 10. In this connection, the front panel 22a and the rear panel 22b define a pair of parallel side edges 24 and 26 and the tear strip 20 is adhesively or otherwise affixed to an inner surface of the sheet material 14 so as to be positioned along one of the two parallel side edges 24 and 26 (i.e., the side edge 24 in FIGS. 1 and 1a).

Still referring to FIGS. 1 and 1a, the seals 16a and 16b joining the confronting proximal end 14a and distal end 14b sheet edges form end seals at opposite ends of the catheter product 12 and the seal 16c joining the confronting side sheet edges 14c forms a single longitudinal seal generally parallel to the catheter product 12. As previously discussed, the sheet material 14 comprises a liquid tight, gas impermeable foil, and thus the end seals 16a and 16b and the single longitudinal seal 16c all are formed as weld seals with one of the end seals 16b being formed longer than the other of the end seal 16a. As shown in FIG. 1, the end seal 16b which is formed longer than the end seal 16a has at least one, and preferably two, finger holes 28 and 30 and a tear line 32 extending from the side edge 26 between and adjacent to the finger holes 28 and 30 to a point adjacent the tear strip 20. With the tear line angled toward the tear strip 20, the end user can use one or both of the finger holes 28 and 30 to propagate the tear line 32 to the tear strip 20 which will thereafter cause the sheet material 14 to tear along the tear strip 20 to thereby cause the package 10 to open along the intended opening line (i.e., the side edge 24).

In one application of the catheter product package 10, the catheter product 12 comprises a catheter 13 having a hydrophilic coating on an insertable portion thereof, and the package 10 includes a wick 33 disposed on an inner surface of the sheet material 14 within the sealed cavity 18. The wick 33 may comprise any suitable wicking material, such as, for example, a fabric strip, an absorbent paper strip, or an absorbent open-celled foam strip. The wick 33 is preferably wetted with an aqueous liquid at a point in time prior to when the sealed cavity 18 is formed by forming the seals 16a, 16b and 16c to thereafter produce a water vapor atmosphere within the sealed cavity 18 for activating the hydrophilic coating on the catheter 13. As shown in FIG. 1, the wick 33 is disposed on and may also be affixed to the inner surface of the sheet material 14 within the sealed cavity 18 to extend in generally parallel relation to the catheter 13 and to the tear strip 20 in a longitudinal direction thereon.

As previously suggested, the catheter 13 extends generally longitudinally within the sealed cavity 18 substantially from a proximal end as at 14a to a distal end as at 14b of the package 10. It will also be appreciated that the sheet material 14 extends from a point beyond the proximal end 12a of the catheter 12 to a point beyond the distal end 12b of the catheter 13. In addition, the package 10 advantageously comprises a continuous seal formed of the pair of end seals 16a and 16b and the single longitudinal seal 16c to define the sealed cavity 18 for the catheter 13.

Comparing FIGS. 1 and 1b, it will be noted that there are striking similarities in construction with a single identifiable distinction and, thus, FIGS. 1 and 1b carry identical reference numerals for identical elements. Among these identical elements are the pair of finger holes 28 and 30 which in both FIG. 1 and FIG. 1a are in longitudinally spaced relation within the longer of the end seals 16b. As for the distinction mentioned above, FIG. 1b includes a tear line 32' having a curved path from one side 26 toward the other side 24 of the package 10 which has a slight curve as at 34 toward and to a point adjacent the tear strip 20.

By including this curve as at 34, one or more of the finger holes 28 and 30 can be used by the end user to better ensure that the tear line 32' will propagate directly to the tear strip 20 to cause the sheet material 14 to tear along the tear strip 20 to thereby cause the package to open along the intended opening line at the side edge 24.

Referring now to FIG. 2, the package 110 for the catheter product 112 comprises a sheet material 114 wrapped about the catheter product 112 in a manner forming a package for the catheter product 112. The catheter product 112 will be seen to comprise a catheter 113 extending generally longitudinally within the package 110, and the sheet material 114 extends from a point beyond the proximal end 112a to a point beyond the distal end 112b of the catheter 113. As described for FIGS. 1 and 1a, the sheet material 114 is wrapped about the catheter 113 to have confronting proximal end 114a and distal end 114b sheet edges and confronting side sheet edges 114c.

Also, as with the embodiment of FIGS. 1 and 1*b*, there is a wick 133 as well as seals 116*a* and 116*b* joining the confronting proximal end 114*a* and distal end 114*b* sheet edges and a single longitudinal seal 116*c* joining the confronting side sheet edges 114*c* of the sheet material 114 to define a sealed cavity 118 for the catheter 113.

In contrast to the embodiment of FIGS. 1 and 1*b*, the front and rear panels define a pair of parallel side edges 124 and 126 wherein a pair of tear strips 120*a* and 120*b* are adhesively or otherwise affixed to an inner surface of the sheet material 114 so that one of the tear strips 120*a* and 120*b* is positioned at each of the side edges 124 and 126, respectively. It will also be seen in FIG. 2 that a pair of finger holes 136 and 138 are provided in laterally spaced relation within the longer of the end seals 116*b* and a tear line 140 having a straight path between the finger holes 136 and 138 branches into two curved paths as at 140*a* and 140*b* toward corresponding tear strips 120*a* and 120*b*. With this arrangement, the end user can use one or both of the finger holes 136 and 138 to cause the tear line 140 to propagate along one or both of the corresponding curved paths 140*a* and 140*b* to the corresponding tear strips 120*a* and 120*b* to thereby cause the package to open along one or both of the intended opening lines defined by the side edges 124 and 126.

Referring to FIGS. 3 and 3*a*, the package 210 for the catheter product 212 comprises the sheet material 214 wrapped about the catheter product 212 in a manner forming a package for the catheter product 212. The catheter product 212 will be seen to comprise a catheter 213 which extends generally longitudinally within the package 210, and the sheet material 214 extends from a point beyond the proximal end 212*a* to a point beyond the distal end 212*b* of the catheter 213. As described for FIG. 2, the sheet material 214 is wrapped about the catheter 213 to have confronting proximal end 214*a* and distal end 214*b* sheet edges and confronting side sheet edges 214*c*.

With this arrangement, and like the embodiments of FIGS. 1, 1*b* and 2, the confronting proximal end 214*a* and distal end 214*b* sheet edges and the confronting side sheet edges 214*c* of the sheet material 214 are sealed as at 216*a*, 216*b*, and 216*c* to define a sealed cavity 218 for the catheter 213.

As shown in FIGS. 3 and 3*a*, the tear strip 220 is adhesively or otherwise affixed to an inner surface of the sheet material 214 so as to be positioned substantially in the middle of the front panel 222*a* where it is disposed substantially directly opposite the single longitudinal seal 216*c* in the middle of the rear panel 222*b*. It will also be seen that a single finger hole 244 is centrally disposed within the longer of the end seals 216*b* and an opening tab 246 is formed in the sealed distal end 214*b* by a slit 248 looping from adjacent the tear strip 220, around the finger hole 244, and back adjacent to the tear strip 220. With this arrangement, the finger hole 244 in the opening tab 246 can be used to further propagate the slit 248 toward the tear strip 220 to cause the sheet material 214 to tear along the tear strip 220 to thereby cause the package to open along the intended opening line defined by the tear strip 220.

Because the tear strip 220 is in the middle of the front panel 222*a*, any liquid within a wick 233 disposed on the inner surface of the rear panel 222*b* will remain captured within the package 210 as the catheter 213 is removed through the opening created by tearing along the tear strip 220. Of course, it is not only desirable for the wick 233 to be disposed on the sheet material 214 within the sealed cavity 218 so as to be positioned on the inner surface of the rear panel 222*b*, but for it to be laterally offset from the single longitudinal seal 216*c* located in the middle of the rear panel 222*b*. By positioning the wick 233 in this manner, the catheter 213 can be removed from the package 210 through the opening in the front panel 222*a* created by tearing along the tear strip 220 while retaining within the package 210 the liquid held within the wick 233.

Referring to FIGS. 4 and 4*a*, the package 310 for the catheter product 312 comprises a sheet material 314 wrapped about the catheter 312 to form a package for the catheter 312. The catheter product 312 will be seen to comprise a catheter 313 which extends generally longitudinally within the package 310, and the sheet material 314 extends from a point beyond the proximal end 312*a* to a point beyond the distal end 312*b* of the catheter 313. As described for FIGS. 3 and 3*a*, the sheet material 314 is wrapped about the catheter 313 to have confronting proximal end 314*a* and distal end 314*b* sheet edges and confronting side sheet edges 314*c*.

As with the embodiments of FIG. 1, 1*a*, 2 and 3 and 3*a*, the confronting proximal end 314*a* and distal end 314*b* sheet edges and the confronting side sheet edges 314*c* of the sheet material 314 are sealed as at 316*a*, 316*b*, and 316*c* to define a sealed cavity 318 for the catheter 313.

Unlike the prior embodiments, the tear strip 350 is adhesively or otherwise affixed to an inner surface of the sheet material 314 within the sealed cavity 318 so as to extend generally perpendicular to the catheter 313 adjacent one of the sealed proximal end 314*a* and sealed distal end 314*b* sheet edges. It will also be seen from FIG. 4*a*, that the package 310 includes a separate seal as at 316*d* along a side edge 324 of the generally rectangular package 310, and the tear strip 350 extends laterally of the package 310 from the seal 316*d* to the opposite side edge 326 thereof. As also shown most clearly in FIG. 4*a*, a pair of slits 346*a* and 346*b* are provided on opposite sides of the tear strip 350 within the seal 316*d* to define an opening tab 352 to tear open the package 310.

With this arrangement, the opening tab 352 can be gripped by the end user and pulled toward the opposite side edge 326 to cause the sheet material 314 to tear along the tear strip 350 to thereby cause the package 310 to open along the intended opening line defined by the tear strip 350.

In the embodiment illustrated in FIG. 4, the end seals 316*a* and 316*b* are of equal length, unlike the end seals in the earlier described embodiments, and the single longitudinal seal 316*c* extends completely from one end seal 316*a* to the other end seal 316*b* to thereby provide a continuous seal. By pulling on the opening tab 352, the tear strip 350 will cause one end of the package 310 to open adjacent one end, e.g., the distal end 312*b* of the catheter 313, following which the catheter can be removed from the package 310 through the open end created by using the opening tab 352 and tear strip 350.

Referring to FIGS. 6 and 6*a*, the package 410 for the catheter product 412 comprises a sheet material 414 wrapped about the catheter product 412 to form a package for the catheter product. The catheter product 412 comprises a catheter 413 which extends generally longitudinally within the package 410, and the sheet material 414 extends from beyond the proximal end 412*a* to beyond the distal end 412*b* of the catheter 413. As described for FIGS. 3 and 3*a*, the sheet material 414 is wrapped about the catheter 413 to have confronting proximal end 414*a* and distal end 414*b* sheet edges and confronting side sheet edges 414*c*.

As with the embodiments of FIGS. 1 and 1*a*, 2, 3 and 3*a*, and 4 and 4*a*, the confronting proximal end 414*a* and distal end 414*b* sheet edges and the confronting side sheet edges 414*c* of the sheet material 414 are sealed as at 416*a*, 416*b*, and 416*c* to define a sealed cavity 418 for the catheter 413.

In the embodiment of FIGS. 6 and 6*a*, a wetted wick 433 is provided and a gas permeable, liquid impermeable barrier 434 is heat sealed to the inner surface of the sheet material 414 to cover the wick 433. This barrier 434 is applied and heat sealed as at 434a and 434b (FIGS. 6a and 6b) to the inner surface of the sheet material 414 shortly after the wick 433 has been wetted with a suitable liquid. In this manner, the sealed cavity 418 formed by the package 410 will have the catheter 413 in one compartment 418a and the liquid used to wet the wick 433 in another compartment 418b whereby the catheter is maintained out of direct contact with the liquid.

In addition, the tear strip 420 is adhesively or otherwise affixed to the heat seal 434a along one of the longitudinal edges of the barrier 434. The compartment 418b containing the wetted wick 433 is liquid tight as a result of the barrier 434 being heat sealed entirely about its perimeter to confine the liquid therein. Thus, the tear strip 420 is affixed within the bounds of the heat seal 434a so the compartment 418b remains liquid tight after opening the package.

The tear strip 420 can be used to cause a tear to propagate along the tear strip and through the heat seal 434a generally along one of the longitudinal edges of the barrier 434. This causes the package 410 to open along an intended opening line which will, in turn, expose only the compartment 418a containing the catheter 413. However, the compartment 418b containing the wetted wick 433 remains liquid tight because the heat seal 434a remains sufficiently intact to preserve this condition.

Still referring to FIGS. 6 and 6a, it will be appreciated that the barrier 434 will run the full length of the package 410 so that opposite ends thereof are captured within the heat seals 416a and 416b. The heat seals 416a and 416b cooperate with the heat seals 434a and 434b to complete the heat sealing of the barrier 434 entirely about its perimeter to thereby form the liquid tight compartment 418b. The package 410 may also have a heat seal such as 435 which serves to prevent possible backflow of liquid during the manufacturing assembly process until such time as the heat seal 416a has been formed.

Figure 7:
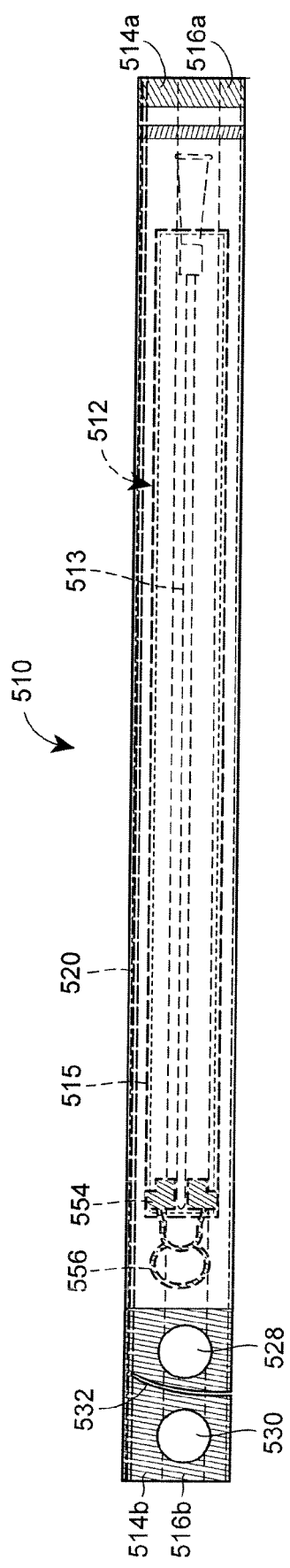
FIG. 7 is a plan view of a sixth embodiment of a catheter product package in accordance with the present disclosure.

Referring to FIG. 7, it will be seen that the package 510 is structurally identical to the package 410 in FIGS. 6 and 6a. The only difference between them is that the package 410 in FIGS. 6 and 6a is shown in use with a catheter product 412 in the form of a catheter 413 having a no-touch sleeve 415 formed of a gas permeable, liquid impermeable material. The no-touch sleeve 415 extends along the hydrophilic coated catheter to cover substantially the entire insertable portion. The package 510 in FIG. 7 is shown in use with a catheter product 512 in the form of a catheter 513 having an insertion tip 554 at one end thereof and also having a no-touch sleeve 515 attached to at least the insertion tip 554. In FIG. 7, the catheter 513 includes a protective cap 556 covering the insertion tip 554 to be removed for using the catheter.

Figure 8A:
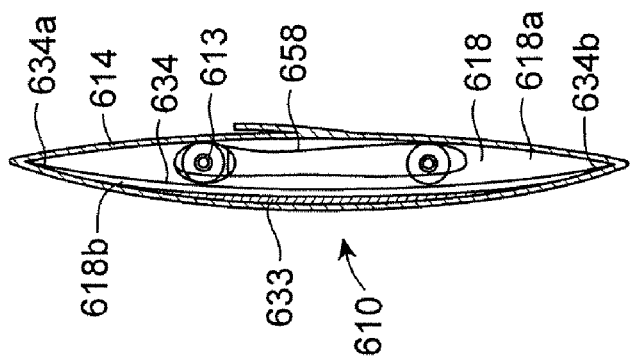
Figure 8:
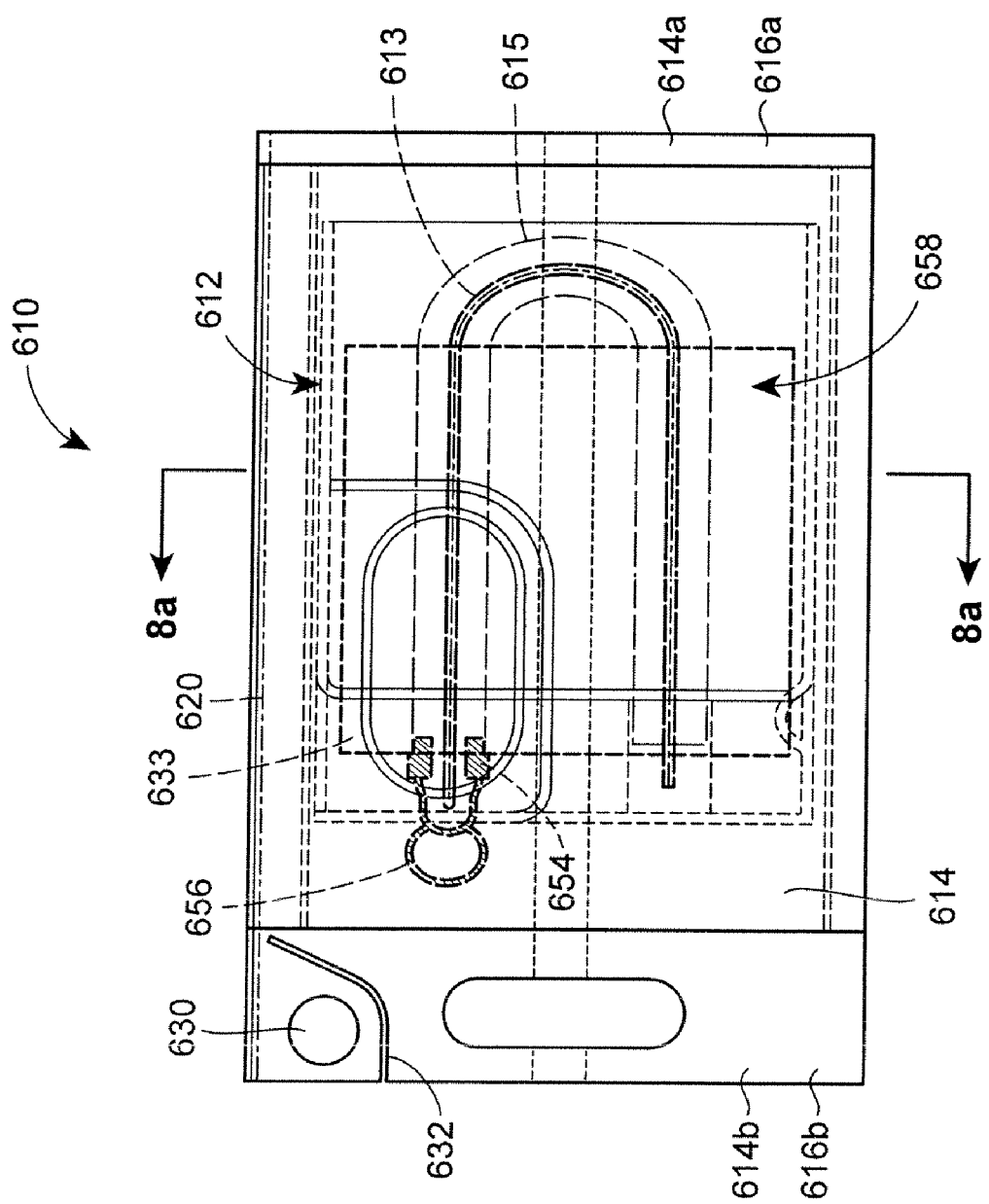
FIG. 8 is a plan view of a seventh embodiment of a catheter product package in accordance with the present disclosure.

Referring to FIGS. 8 and 8a, it will be seen that the package 610 is also almost entirely structurally identical to the package 410 in FIGS. 6 and 6a and the package 510 in FIG. 7. The primary difference is that the package 410 in FIGS. 6 and 6a is shown in use with a catheter product 412 in the form of a hydrophilic coated catheter 413 having a no-touch sleeve 415 whereas the catheter product 612 comprises a hydrophilic coated catheter 613 assembled within, and as a part of, a urine collection bag assembly 658. The package 610 is still generally rectangular in shape, but the ratio of length to width will be considerably less than for the packages 410 and 510 which are designed for use with a catheter alone.

In other words, the package 610 has a size and shape to accommodate the typical size and shape of a urine collection bag assembly such as 658. Unlike the long, narrow shape of typical catheter-only packages such as 410 and 510, the catheter 613 is folded into a generally U-shape within the collection bag assembly 658 (see FIG. 8) to form the urine collection bag assembly thereby requiring a shorter but wider package for the assembly due to the shape of the collection bag. While not important to the packaging, it will be seen that the catheter 613 in the assembly 658 has a no-touch sleeve 615, an insertion tip 654, and a protective cap 656.

As will also be appreciated from the embodiments of FIGS. 6, 6a, 6b; 7; and 8, 8a, they have other features of the respective catheter packages 410, 510, 610 in common with the earlier described catheter packages 10, 110, 210, and 310. In particular, it will be noted that the respective catheter packages 410, 510, 610 have confronting proximal end (414a, 514a, 614a) and distal end (414b, 514b, 614b) sheet edges which are sealed (as at 416a, 516a, 616a and 416b, 516b, 616b, respectively), and they also have respective tear lines (432, 532, 632) leading to respective tear strips (420, 520, 620) which may be substantially as shown in the drawings. Further, the catheter packages 410, 510, 610 have respective finger hole(s) (428, 430; 528; 530; 630) to assist the end user in opening the packages.

With regard to all of the aforementioned embodiments and features, it will be understood that they are useful for all catheter product packages regardless of the exact size and shape and whether or not they are formed to hold catheters alone or to hold urine collection bag assemblies that incorporate a catheter therein. Thus, it will also be seen from FIGS. 8 and 8a that a wetted wick 633 is used to activate a hydrophilic coating on the catheter 613, and a gas permeable, liquid impermeable barrier 634 is heat sealed as at 634a and 634b to the inner surface of the sheet material 614 in a manner which is sufficient to cover the wetted wick 633. In this manner, the sealed cavity 618 formed by the package 610 will have the urine collection bag assembly 658 in one compartment 618a and the liquid used to wet the wick in another compartment 618b whereby the hydrophilic coated catheter 613 is maintained out of direct contact with the liquid.

As will be appreciated, the collection bag 658 will be formed of a gas permeable, liquid impermeable material to permit vapor produced by a change of phase of the liquid in the wick 633 to pass through the gas permeable barrier 634, through the gas permeable collection bag, and through the no-touch sleeve 615 to hydrate the hydrophilic coating on the catheter 613.

Referring to FIG. 5, the apparatus 60 can be utilized to perform an automated method of forming packages for catheters wherein a roll of sheet material 62 is provided on a reel holder 64 for forming the packages. The sheet material is advanced from the roll 62 in a flat form as at 66 toward a catheter product receiving point 68. A tear strip is affixed as at 70 to the sheet material as it advances in a flat form as at 66 toward the catheter receiving point 68. In one application, the catheter products comprise catheters which have a hydrophilic coating in which case the method includes affixing or otherwise disposing a wick, such as a length of fabric, as at 78 on a surface of the sheet material. The method also may include wetting the wick as at 80 with an aqueous liquid such as liquid water. A gas permeable, liquid impermeable barrier is then deposited over the wick and heat sealed as at 81 to the inner surface of the sheet material, thus sealing the wetted wick between the inner surface of the sheet material and the gas permeable, liquid impermeable barrier.

The sheet material having the gas permeable, liquid impermeable barrier sealed thereto is then wrapped into a U-shape to receive the catheter products at the catheter product receiving point 68. The catheter products traveling on the infeed conveyor 72 are placed on the U-shaped sheet material (or, more precisely, onto an exposed surface of the gas permeable, liquid impermeable barrier) one at a time at the catheter product receiving point 68, and the sheet material is further wrapped about each of the catheter products. The further wrapping of the sheet material forms a cavity for the catheter products. The sheet material is sealed as at 74 in a manner forming a separate, sealed cavity for each of the catheter products, following which the sheet material is cut as at 76 in a manner forming a separate, distinct package for each of the catheter products.

In each of the distinct packaged catheter products, as the liquid associated with the wick changes phase from a liquid to a vapor, the resulting vapor is able to pass through the gas permeable, liquid impermeable barrier, and activate the hydrophilic coating of the catheter.

In addition, the step of affixing a tear strip on the sheet material preferably includes affixing the strip as at 70 so as to extend generally parallel to the catheter products within the sealed cavities.

The sheet material preferably comprises a liquid tight, gas impermeable foil, the tear strip is formed of a suitable material such as polyester having a polyethylene backing, and the tear strip is adhesively or otherwise affixed in position on the inner surface of the sheet material. The foil preferably has sufficient tear propagation properties, as may be provided by having a sufficient aluminum content, so that tearing in the direction of the tear strip causes the tear to thereafter propagate along the tear strip to cause the packages to open along an intended opening line.

As will also be appreciated, the step of sealing the sheet material for each package includes forming a seal extending generally parallel to the catheter product and forming a seal extending generally perpendicular to the catheter product at each of opposite ends thereof. In particular, the step of sealing the sheet material includes forming a longitudinal seal along the length of the catheter product and forming an end seal at each of opposite ends of the catheter product to form the sealed cavity therefor. Preferably, with the sheet material being comprised of a liquid tight, gas impermeable foil, the longitudinal seal and the end seals all are formed as weld seals with one of the end seals being formed longer than the other of the end seals.

As will also be appreciated, the step of sealing the sheet material therefore preferably includes forming a single longitudinal seal generally parallel to the catheter product and forming a pair of end seals generally perpendicular to the catheter product beyond opposite ends thereof. The catheter product and the tear strip are both preferably placed on a common surface of the sheet material (or, in certain embodiments, the catheter is separated from the inner surface of the sheet material by a gas permeable, liquid impermeable barrier) and the tear strip is of a length so as to extend continuously through each of the end seals in such a manner as to be generally parallel to the single longitudinal seal and the catheter product. Moreover, one of the end seals will be understood to be formed in such a manner as to be longer than the other of the end seals, wherein the longer end seal is suitably provided with a finger hole and a tear line extending from adjacent the finger hole to adjacent the tear strip.

By using the described materials and sealing techniques, the present disclosure eliminates the need for two sheets of material joined by a seal which extends entirely about the perimeter of the package. This ensures a compact package wherein only a single sheet of material is used and in which a pair of end seals must cooperate with only a single longitudinal seal to ensure the cavity containing the catheter product remains sealed until the end user decides to open the package to use the catheter product.

In another respect, the catheter product package may be constructed of two sheets of material which are sealed about their perimeters to define a catheter product-receiving sealed cavity, or it may be constructed of a vacuum or thermo formed plastic material to define a cavity sealed with a sheet material. A tear strip may advantageously be affixed to the sheet material to cause it to tear along the tear strip so the package opens along an intended opening line whereby the tear strip extends from a perimeter seal to a point within the sealed cavity to facilitate removal of the catheter product from the package for use. Preferably, the tear strip is secured adhesively or by heat sealing it to an inner surface of the sheet material, and the sheet material is formed of foil or some other material having suitable linear tear propagation tendencies to cause the package to be opened along the intended opening line.

With regard to these alternative forms of catheter product package, it will be appreciated that these are additional potential tear strip embodiments using the concepts of the illustrated and described embodiments. The only difference would lie in the catheter product package either being in the form of a conventional catheter product package formed of two sheets of material sealed about their perimeters or in the form of a vacuum or thermo formed plastic material sealed with a sheet material in place of the wrapped configuration which is fully illustrated and described hereinabove. By forming seals and placing tear lines and tear strips as shown and described herein, the benefits of the tear strips can be realized in any catheter product package for those possessing a limited degree of manual dexterity.

While in the foregoing, preferred embodiments of the present disclosure have been set forth, it will be appreciated that the details herein given may be varied by those skilled in the art without departing from the true spirit and scope of the appended claims.

What is claimed is:

1. A combination of a catheter and a package, comprising:
    a catheter having a proximal end, a distal end, and a hydrophilic coating;
    a sheet material wrapped about the catheter to form a package, the catheter extending generally longitudinally within the package, the sheet material extending from beyond the proximal end to beyond the distal end of the catheter;
    the sheet material being wrapped about the catheter to have confronting proximal end and distal end sheet edges and confronting side sheet edges;
    a seal joining the confronting proximal end and distal end sheet edges and the confronting side sheet edges of the sheet material to define a sealed cavity for the catheter; and
    a gas permeable, liquid impermeable barrier disposed within the package, the barrier dividing the sealed cavity into a first compartment within which the catheter is contained and a second compartment within which a wick wetted with an aqueous liquid is entirely confined.

2. The package of claim 1 including a tear strip affixed to the sheet material to cause the sheet material to tear along the tear strip to thereby cause the package to open along an intended opening line, the tear strip disposed along a portion of the sheet material that, together with the barrier, defines the first compartment.

3. The package of claim 2 wherein the tear strip extends within the sealed cavity in a desired direction relative to the catheter to cause the package to open along the intended opening line in a manner facilitating removal of the catheter from the package for use.

4. The package of claim 2 wherein the tear strip is affixed to an inner surface of the sheet material within the sealed cavity and extends from the sealed proximal end to the sealed distal end sheet edges in generally parallel relation to the catheter.

5. The package of claim 4 wherein the sheet material comprises a liquid tight, gas impermeable foil and the tear strip affixed in position within the sealed cavity on the inner surface of the sheet material.

6. The package of claim 2 wherein the tear strip is affixed to an inner surface of the sheet material within the sealed cavity and extends adjacent and generally parallel to one of the sealed proximal end and sealed distal end sheet edges.

7. The package of claim 6 wherein the sheet material comprises a liquid tight, gas impermeable foil and the tear strip is formed of polyester, has a polyethylene backing, and is affixed in position within the sealed cavity on the inner surface of the sheet material.

8. The package of claim 2 wherein the package is of a generally rectangular shape, the sheet material is wrapped about the catheter and sealed to define a front panel and a rear panel, and a longitudinal seal is formed in the middle of the rear panel.

9. The package of claim 8 wherein the tear strip is affixed to an inner surface of the sheet material so as to be positioned in the middle of the front panel so as to be directly opposite the longitudinal seal formed in the middle of the rear panel.

10. The package of claim 8 wherein the front and rear panels define a pair of parallel side edges and including a pair of tear strips affixed to an inner surface of the sheet material so that one of the tear strips is positioned at each of the side edges.

11. The package of claim 2 wherein the seal joining the confronting side sheet edges forms a longitudinal seal parallel to the catheter and the seals joining the confronting proximal end and distal end sheet edges form end seals generally perpendicular to the catheter.

12. The package of claim 11 wherein the sheet material comprises a liquid tight, gas impermeable foil, the longitudinal seal and the end seals all being formed as weld seals, and with one of the end seals being formed longer than the other of the end seals.

13. The package of claim 11 wherein one of the end seals is formed longer than the other of the end seals, the longer of the end seals having at least one finger hole and a tear line extending from adjacent the finger hole to adjacent the tear strip.

14. The package of claim 2 wherein the wick is disposed on the inner surface of the sheet material within the sealed cavity to extend in generally parallel relation to the catheter and the tear strip in a longitudinal direction thereon.

15. The package of claim 1 wherein the hydrophilic coating is on at least an insertable portion of the catheter and the catheter is disposed so as to extend in a generally longitudinal direction within the package.

16. The package of claim 15 wherein the catheter includes a no-touch sleeve formed of a gas permeable material and extending along the catheter to cover substantially the entire insertable portion having the hydrophilic coating thereon.

17. The package of claim 16 wherein the catheter further includes an insertion tip at one end thereof, the no-touch sleeve being attached to at least the insertion tip, and the insertion tip includes a protective cap to be removed for using the catheter.

18. The package of claim 1 wherein the catheter includes a hydrophilic coating on an insertable portion thereof and the catheter is disposed within a urine collection bag so as to extend in a generally U-shape.

19. The package of claim 18 wherein the urine collection bag is formed of a gas permeable, liquid impermeable material, the catheter includes a no-touch sleeve formed of a gas impermeable material, and the urine collection bag is generally rectangular in shape.

20. The package of claim 1, wherein the barrier is heat sealed to an inner surface of the sheet material.

21. The package of claim 1, wherein the wick is disposed on an inner surface of the sheet material.

22. A combination of a catheter and a package, comprising:
a catheter having a proximal end, a distal end, and a hydrophilic coating;
a sheet material wrapped about the catheter to form a generally rectangular package, the catheter extending generally longitudinally and substantially from a proximal end to a distal end of the package, the sheet material extending from beyond the proximal end of the catheter to beyond the distal end of the catheter;
the sheet material being wrapped about the catheter to have confronting proximal end and distal end sheet edges and confronting side sheet edges;
a continuous seal formed of: (i) a pair of end seals joining the confronting proximal end and distal end sheet edges of the sheet material and (ii) a longitudinal seal joining the confronting side sheet edges of the sheet material, to define a sealed cavity for the catheter; and
a gas permeable, liquid impermeable barrier disposed within the package, the barrier dividing the sealed cavity into a first compartment within which the catheter is contained and a second compartment within which a wick wetted with an aqueous liquid is entirely confined.

23. The package of claim 22 including a tear strip affixed to the sheet material to cause the sheet material to tear along the tear strip to thereby cause the package to open along an intended opening line; the tear strip disposed along a portion of the sheet material that, together with the barrier, defines the first compartment.

24. The package of claim 23 wherein one of the end seals is formed longer than the other of the end seals, the longer of the end seals having at least one finger hole and a tear line extending from adjacent the finger hole to adjacent the tear strip.

25. The package of claim 24 including a pair of finger holes in longitudinally spaced relation within the longer of the end seals and a tear line having a curved path from one side toward the other side of the package to a point adjacent the tear strip.

26. The package of claim 24 wherein the sheet material is wrapped about the catheter and sealed to define a front panel and a rear panel, and a longitudinal seal being formed in the middle of the rear panel and extending from one end seal to the other end seal.

27. The package of claim 26 wherein the front and rear panels define a pair of parallel side edges and including a pair of tear strips affixed to an inner surface of the sheet material so that one of the tear strips is positioned at each of the side edges.

28. The package of claim 27 including a pair of finger holes in laterally spaced relation within the longer of the end seals and a tear line having a straight path between the finger holes branching into two curved paths to points adjacent the respective tear strips.

29. The package of claim 26 wherein the tear strip is affixed to an inner surface of the sheet material so as to be positioned in the middle of the front panel so as to be directly opposite the longitudinal seal formed in the middle of the rear panel.

30. The package of claim 29 wherein the finger hole is centrally disposed in the front panel within the longer of the end seals in an opening tab formed by a slit looping from adjacent the tear strip, around the finger hole, and back adjacent to the tear strip.

31. The package of claim 23 including a separate seal along an edge of the generally rectangular package, the tear strip extending laterally of the package from the seal to the opposite edge thereof, and including a pair of slits on opposite sides of the tear strip within the seal to define an opening tab to tear open the package.

32. The package of claim 22, wherein the barrier is heat sealed to an inner surface of the sheet material.

33. The package of claim 21, wherein the wick is affixed to the inner surface of the sheet material.

34. The package of claim 22, wherein the wick is disposed on an inner surface of the sheet material.

35. The package of claim 34, wherein the wick is affixed to the inner surface of the sheet material.

36. The package of claim 34, wherein the wick extends in a longitudinal direction on the inner surface of the sheet material, in generally parallel relation to the catheter.

37. A combination of a catheter and a package for the catheter, comprising:
 a catheter having a hydrophilic coating;
 a sealed cavity for the catheter defined at least in part by a sheet material;
 a gas permeable, liquid impermeable barrier disposed within the package, the barrier dividing the sealed cavity into a first compartment within which the catheter is contained and a second compartment within which a wick wetted with an aqueous liquid is entirely confined; and
 a tear strip affixed to the sheet material on a side of the sheet material that, together with the barrier, defines the first compartment;
 the tear strip causing the sheet material to tear along an intended opening line.

38. The package of claim 37 including a seal associated with the sheet material defining at least in part the sealed cavity for the catheter.

39. The package of claim 38 wherein the tear strip extends from the seal to a point overlying the sealed cavity to facilitate catheter removal.

40. The package of claim 39 wherein the tear strip is affixed to an inner surface of the sheet material so as to face the cavity for the catheter.

41. The package of claim 40 wherein the sheet material is formed of a material characterized by linear tear propagation tendencies.

42. The package of claim 38 wherein the seal associated with the sheet material has at least one finger hole extending therethrough.

43. The package of claim 42 wherein the tear line extends from a point adjacent the finger hole to a point adjacent the tear strip.

44. The package of claim 37, wherein the barrier is heat sealed to an inner surface of the sheet material.

45. The package of claim 21, wherein the wick extends in a longitudinal direction on the inner surface of the sheet material, in generally parallel relation to the catheter.

46. The package of claim 37, wherein the wick is disposed on an inner surface of the sheet material.

47. The package of claim 46, wherein the wick is affixed to the inner surface of the sheet material.

48. The package of claim 46, wherein the wick extends in a longitudinal direction on the inner surface of the sheet material, in generally parallel relation to the catheter.

* * * * *